United States Patent
Banks et al.

(10) Patent No.: US 9,207,221 B2
(45) Date of Patent: *Dec. 8, 2015

(54) METHODS OF DETECTING REVERSE TRIIODOTHYRONINE BY MASS SPECTROMETRY

(71) Applicant: Quest Diagnostics Investments, Inc., San Clemente, CA (US)

(72) Inventors: J. Fred Banks, San Juan Capistrano, CA (US); Peter P. Chou, San Juan Capistrano, CA (US); Noriya M. Matt, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/533,900

(22) Filed: Nov. 5, 2014

(65) Prior Publication Data

US 2015/0308991 A1    Oct. 29, 2015

Related U.S. Application Data

(63) Continuation of application No. 14/445,675, filed on Jul. 29, 2014, now Pat. No. 8,890,061, which is a continuation of application No. 14/190,313, filed on Feb. 26, 2014, now Pat. No. 8,963,077, which is a continuation of application No. 13/311,412, filed on Dec. 5, 2011, now Pat. No. 8,669,519.

(51) Int. Cl.
*H01J 49/26* (2006.01)
*H01J 49/00* (2006.01)
*G01N 33/53* (2006.01)
*G01N 30/72* (2006.01)

(Continued)

(52) U.S. Cl.
CPC ............ *G01N 30/7233* (2013.01); *G01N 33/78* (2013.01); *H01J 49/0031* (2013.01); *H01J 49/0431* (2013.01); *G01N 2560/00* (2013.01)

(58) Field of Classification Search
USPC ......... 250/281–283, 287–290, 293, 294, 298, 250/299, 423 R, 424, 425; 210/281–283, 210/287–290, 293, 294, 298, 299, 423 R, 210/424, 425; 422/70, 68.1, 528; 436/161, 436/169, 171, 173, 174, 179–181, 500

See application file for complete search history.

(56) References Cited

U.S. PATENT DOCUMENTS

| | | |
|---|---|---|
| 5,288,644 A | 2/1994 | Beavis et al. |
| 5,772,874 A | 6/1998 | Quinn et al. |

(Continued)

FOREIGN PATENT DOCUMENTS

WO    2012087438 A1    6/2012

OTHER PUBLICATIONS

Couldwell A.M., et al., "Tandem Mass Spectrometry of Deprotonated Iodothyronines," Rapid Communications in Mass Spectrometry, 2005, vol. 19 (16), pp. 2295-2304.

(Continued)

*Primary Examiner* — Bernard E Souw
(74) *Attorney, Agent, or Firm* — Quest Diagnostics, Inc.

(57) ABSTRACT

Provided are methods for determining the amount of reverse T3 in a sample using mass spectrometry. The methods generally involve ionizing reverse T3 in a sample and detecting and quantifying the amount of the ion to determine the amount of reverse T3 in the sample.

24 Claims, 12 Drawing Sheets

(51) Int. Cl.
*H01J 49/04* (2006.01)
*G01N 33/78* (2006.01)

(56) References Cited

U.S. PATENT DOCUMENTS

| | | | |
|---|---|---|---|
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koester | |
| 7,618,827 B2 | 11/2009 | Soldin et al. | |
| 8,227,259 B2 | 7/2012 | Soldin | |
| RE44,401 E | 7/2013 | Soldin | |
| 2004/0006026 A1* | 1/2004 | Weitnauer | C07H 9/02 514/25 |
| 2004/0235188 A1* | 11/2004 | Soldin | G01N 33/6848 436/500 |
| 2005/0164402 A1 | 7/2005 | Belisle et al. | |
| 2006/0223188 A1* | 10/2006 | Soldin | G01N 33/6848 436/86 |
| 2011/0070659 A1 | 3/2011 | Belisle et al. | |
| 2011/0282587 A1* | 11/2011 | Jones | H01J 49/0036 702/19 |
| 2012/0132797 A1* | 5/2012 | Strauss | G01N 33/6893 250/282 |
| 2012/0309105 A1 | 12/2012 | Soldin | |

OTHER PUBLICATIONS

Friberg L., et al., "Rapid Down-regulation of Thyroid Hormones in Acute Myocardial Infarction," Archives of Internal Medicine, 2002, vol. 162 (12), pp. 1388-1394.

Hantson A.L., et al., "Simultaneous Determination of Endogenous and 13C-Labeled Thyroid Hormones in Plasma by Stable Isotope Dilution Mass Spectrometry," Journal of Chromatography B, 2004, vol. 807 (2), pp. 185-192.

International Preliminary Report and Written Opinion on Patentability for Application No. PCT/US2012/067338, mailed on Feb. 26, 2013.

International Search Report for Application No. PCT/US2012/067338, mailed on Feb. 26, 2013, 4 Pages.

Kunisue T., et al., "A Method for the Analysis of Six Thyroid Hormones in Thyroid Gland by Liquid Chromatography—Tandem Mass Spectrometry," Journal of Chromatography B, 2010, vol. 878 (21), pp. 1725-1730.

Merchant M., et al., "Recent Advancements in Surface-Enhanced Laser Desorption/Ionization-Time of Flight-Mass Spectrometry," Electrophoresis, 2000, vol. 21 (6), pp. 1164-1177.

Robb D.B., et al., "Atmospheric Pressure Photoionization: An Ionization Method for Liquid Chromatography—Mass Spectrometry," Analytical Chemistry, 2000, vol. 72 (15), pp. 3653-3659.

Tai S.S., et al., "Development and Evaluation of a Reference Measurement Procedure for the Determination of Total 3, 3', 5-Triiodothyronine in Human Serum Using Isotope-Dilution Liquid Chromatography—Tandem Mass Spectrometry," Analytical Chemistry, 2004, vol. 76 (17), pp. 5092-5096.

Thienpont L.M., et al., "Isotope Dilution-Gas Chromatography/Mass Spectrometry and Liquid Chromatography/Electrospray Ionization—Tandem Mass Spectrometry for the Determination of Triiodo-L-Thyronine in Serum," Rapid Communications in Mass Spectrometry, 1999, vol. 13 (19), pp. 1924-1931.

Wang D., et al., "Analysis of Thyroid Hormones in Serum by Liquid Chromatographytandem Mass Spectrometry," Analytical and Bioanalytical Chemistry, 2010, vol. 397 (5), pp. 1831-1839.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Zhang Y., et al., "Detection and Quantification of 3,5,3'-Triiodothyronine and 3,3',5'-Triiodothyronine by Electrospray Inoization Tandem Mass Spectrometry," Journal of Mass Spectrometry, 2005, vol. 16 (11), pp. 1781-1786.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography—Tandem Mass Spectrometry," Journal of Chromatography A, 1999, vol. 854, pp. 23-25.

* cited by examiner

METHODS OF DETECTING REVERSE TRIIODOTHYRONINE BY MASS SPECTROMETRY

CROSS-REFERENCE TO RELATED APPLICATIONS

This application is a continuation application of U.S. non-provisional application Ser. No. 14/445,675, filed Jul. 29, 2014, now U.S. Pat. No. 8,890,061, which is a continuation of U.S. non-provisional application Ser. No. 14/190,313, filed Feb. 26, 2014, now U.S. Pat. No. 8,963,077, which is a continuation application of U.S. non-provisional application Ser. No. 13/311,412, filed Dec. 5, 2011, now U.S. Pat. No. 8,669,519, the contents of which are hereby incorporated by reference in its their entirety into this application.

FIELD OF THE INVENTION

The invention relates to the detection of reverse triiodothyronine. In a particular aspect, the invention relates to methods for detecting reverse triiodothyronine by mass spectrometry.

BACKGROUND OF THE INVENTION

The following description of the background of the invention is provided simply as an aid in understanding the invention and is not admitted to describe or constitute prior art to the invention.

Reverse triiodothyronine ((2S)-2-amino-3-[4-(4-hydroxy-3,5-diiodophenoxy)-3-iodophenyl]propanoic acid) (rT3) is a non-active isomer of triiodothyronine (T3). T3 and rT3 are both derived from thyoxine (T4) through the action of deiodinase as follows:

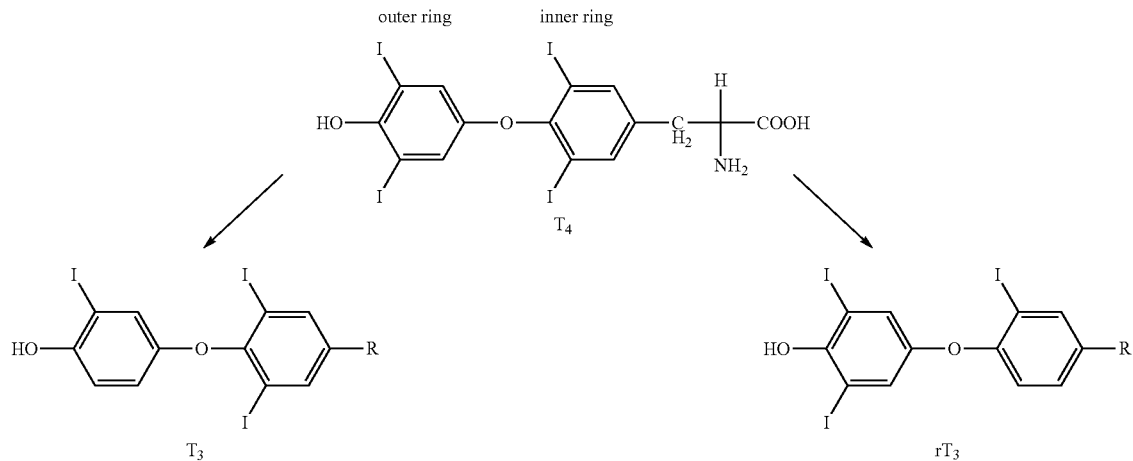

Both T3 and rT3 bind to thyroid hormone receptors. When T3 binds, the receptors are stimulated, thus increasing metabolic activity. Upon binding, rT3, unlike T3, does not stimulate thyroid hormone receptors. Thus, rT3 does not stimulate metabolic activity of the target cell, and in fact, blocks receptor sites from T3 activation.

An excess if rT3 may result in widespread shutdown in T3 binding, a condition called reverse T3 dominance. Reverse T3 dominance results in reduced body temperature, which slows the action of many enzymes, leading to a clinical syndrome, Multiple Enzyme Dysfunction, which produces the effects seen in hypothyroidism.

Further, the process of 5' monodeiodination that converts T4 to T3, and rT3 to diiodothyronine (DIT) is inhibited in a wide variety of conditions, including fasting, malnutrition, poorly controlled diabetes mellitus, trauma, surgery, and systemic illness. Consequently, the serum T3 level typically decreases, and the rT3 level often increases in these circumstances. Thus, the ratio of T3 to rT3 is an important diagnostic marker for the metabolism and function of thyroid hormones and related compounds in clinical chemistry.

Assays for T4, T3, and related compounds (including rT3) have been developed and are used to evaluate thyroid status or to optimize therapeutic dosages. Assay formats include radioimmunoassay and mass spectrometry. For example, Hantson et al. reported quantitating derivatized thyroid hormones via GC-MS (Hansen et al., J. Chromatogr. B (2004), 807:185-192); Zhang et al. reported quantitating T3 and rT3 in human serum via SPE-ESI-MS/MS (Zhang et al., J. Am. Soc. Mass Spectrom. (2005), 16:1781-86); Tai et al. reported quantitating T3 in serum via SPE-HPLC-MS/MS (Tai et al., Anal. Chem. (2004), 76:5092:96); Couldwell et al. report mass spectrometric analysis, including fragmentation spectra, of rT3 in standard organic solvents by ESI-MS/MS (Couldwell et al., Rapid Comm. Mass Spectrom. (2005), 19:2295-2304); Wang and Stapleton report quantitation of rT3 in spiked bovine serum samples via SPE-LC-ESI-MS/MS (Wang and Stapleton, Anal Bioanal Chem (2010), 397:1831-39).

SUMMARY OF THE INVENTION

The present invention provides methods for detecting the amount of reverse T3 (rT3) in a sample by mass spectrometry, including tandem mass spectrometry.

In one aspect, methods are provided for determining the amount of rT3 in a body fluid sample by mass spectrometry. Methods of this aspect include: (a) ionizing rT3 from the body fluid sample to produce one or more rT3 ions detectable by mass spectrometry; and (b) detecting the amount of the rT3 ion(s) by mass spectrometry. Once the amount of the one or more rT3 ions is measured, the amount of rT3 ion(s) determined is related to the amount of rT3 in the body fluid sample. In some methods of the present invention, rT3 from the body fluid sample is not subjected to solid phase extraction prior to ionization.

In some embodiments, rT3 from the body fluid sample is subjected to liquid chromatography prior to being ionized. In some embodiments, the liquid chromatography comprises high performance liquid chromatography (HPLC).

In some embodiments, rT3 from the body fluid sample is enriched by protein precipitation prior to being ionized. In some embodiments, the protein precipitation is conducted prior to liquid chromatography. In some embodiments, protein precipitation is conducted by contacting the body fluid sample with an organic solvent in an amount sufficient to precipitate at least a portion of protein that may be present in the body fluid sample. In some related embodiments, the organic solvent comprises methanol.

In some embodiments, methods determining the amount of reverse T3 (rT3) in a body fluid sample by mass spectrometry are provided which include processing a body fluid sample to generate a processed sample comprising rT3 from a body fluid sample. In related methods, the processing comprises: i) precipitating protein from the body fluid sample by adding an organic solvent, such that the resulting supernatant comprises the organic solvent and rT3 from the body fluid sample; ii) purifying rT3 in the supernatant by subjecting the supernatant to a reverse-phase high performance liquid chromatography (RP-HPLC) column, wherein the purifying comprises introducing an aqueous solution to the column immediately prior to introducing the supernatant; and iii) eluting rT3 from the RP-HPLC column to generate a processed sample comprising rT3. This processed sample may then be analyzed as described above; namely, by ionizing rT3 in the processed sample to generate one or more reverse T3 ions detectable by mass spectrometry; determining the amount of one or more rT3 ions by mass spectrometry; and using the amount of the determined rT3 ions to determine the amount of rT3 in the body fluid sample. In some embodiments, the organic solvent comprises methanol. In some related embodiments, the supernatant generated in step ii) comprises at least 10% methanol In embodiments where an aqueous plug is introduced into an RP-HPLC column prior to introduction of an rT3-containing sample, the ratio of the sample volume to the aqueous plug volume may be within the range of about 10:1 to about 1:10; such as within the range of about 5:1 to about 1:5; such as about 1:1.

In some embodiments, one or more rT3 ions detectable by mass spectrometry are selected from the group consisting of ions with a mass/charge ratio of 649.9±0.5, 605.2±0.5, and 127.1±0.5. In some embodiments, the ions are selected from the group consisting of ions with a mass/charge ratio of 649.9±0.5 and 605.2±0.5.

In some embodiments, mass spectrometry comprises tandem mass spectrometry. In some related embodiments, one or more rT3 ions detectable by mass spectrometry comprise a precursor ion with a mass/charge ratio of 649.9±0.5, and a fragment ion selected from the group of ions with a mass/charge ratio of 605.2±0.5 and 127.1±0.5. In some embodiments, the fragment ion has a mass/charge ratio of 605.2±0.5.

In some embodiments, the body fluid sample comprises plasma or serum, such as plasma or serum taken from a human. In some related embodiments, the methods described herein may be used to determine the amount of rT3 present in a plasma or serum sample when taken from a human.

In certain embodiments of the methods disclosed herein, mass spectrometry is performed in negative ion mode. Alternatively, mass spectrometry is performed in positive ion mode. Various ionization sources, including for example atmospheric pressure chemical ionization (APCI) or electrospray ionization (ESI), may be used in embodiments of the present invention. In certain embodiments, rT3 is measured using ESI in negative ion mode.

In some embodiments, a separately detectable internal rT3 standard is provided in the sample, the amount of which is also determined in the sample. In these embodiments, all or a portion of both the endogenous rT3 and the internal standard present in the sample is ionized to produce a plurality of ions detectable in a mass spectrometer, and one or more ions produced from each are detected by mass spectrometry.

A preferred internal rT3 standard is $^{13}C_6$-rT3. In preferred embodiments, the internal rT3 standard ions detectable in a mass spectrometer are selected from the group consisting of negative ions with m/z of 655.8±0.50 and 611.1±0.50. In embodiments utilizing tandem mass spectrometry, $^{13}C_6$-rT3 ions may comprise a precursor ion with m/z of 655.8±0.50 and a fragment ion with m/z of 611.1±0.50.

In preferred embodiments, the presence or amount of the rT3 ion is related to the presence or amount of rT3 in the test sample by comparison to a reference such as $^{13}C_6$-rT3.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected rT3 parent or daughter ions by mass spectrometry. Relative reduction as this term is used does not require that any substance, present with the analyte of interest in the material to be purified, is entirely removed by purification.

As used herein, the term "test sample" refers to any sample that may contain rT3. As used herein, the term "body fluid" means any fluid that can be isolated from the body of an individual. For example, "body fluid" may include blood, plasma, serum, bile, saliva, urine, tears, perspiration, and the like.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and high turbulence liquid chromatography (HTLC).

As used herein, the term "high performance liquid chromatography" or "HPLC" refers to liquid chromatography in which the degree of separation is increased by forcing the mobile phase under pressure through a stationary phase on a support matrix, typically a densely packed column.

As used herein, the term "high turbulence liquid chromatography" or "HTLC" refers to a form of chromatography that utilizes turbulent flow of the material being assayed through the column packing as the basis for performing the separation. HTLC has been applied in the preparation of samples containing two unnamed drugs prior to analysis by mass spectrometry. See, e.g., Zimmer et al., *J. Chromatogr. A* 854: 23-35 (1999); see also, U.S. Pat. Nos. 5,968,367, 5,919,368, 5,795,469, and 5,772,874, which further explain HTLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 35 µm. As used in this context, the term "about" means ±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 2.6 µm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LLOQ is identifiable, discrete and reproducible with a concentration at which the standard deviation (SD) is less than one third of the total allowable error (TEa; arbitrarily set for rT3 as 30% of the LLOQ).

As used herein, the term "limit of detection" or "LOD" is the point at which the measured value is larger than the uncertainty associated with it. The LOD is the point at which a value is beyond the uncertainty associated with its measurement and is defined as the mean of the blank plus four times the standard deviation of the blank.

As used herein, an "amount" of rT3 in a body fluid sample refers generally to an absolute value reflecting the mass of rT3 detectable in volume of body fluid. However, an amount also contemplates a relative amount in comparison to another rT3 amount. For example, an amount of rT3 in a body fluid can be an amount which is greater than a control or normal level of rT3 normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 1A shows the loading phase (i.e., loading of a sample loop).

DETAILED DESCRIPTION OF THE INVENTION

Figure 1A:
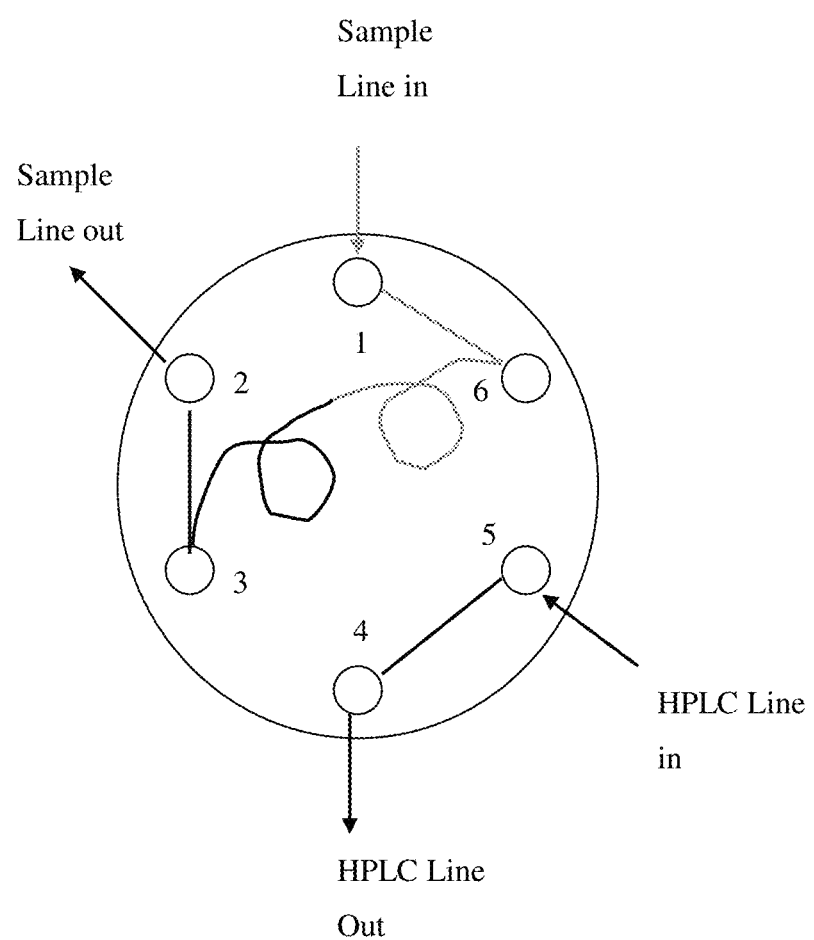
FIGS. 1A and B show schematic diagrams of HPLC pump configurations which result in introduction of an aqueous plug immediately prior to introduction of the sample. Aqueous solvents are shown in black, while the sample with high organic solvent content is shown in grey.

Methods of the present invention are described for measuring the amount of rT3 in a sample. More specifically, mass spectrometric methods are described for detecting and quantifying rT3 in a sample. The methods may utilize liquid chromatography (LC), most preferably HPLC, to perform a purification of selected analytes, and combine this purification with unique methods of mass spectrometry (MS), thereby providing a high-throughput assay system for detecting and quantifying rT3 in a test sample. The preferred embodiments are particularly well suited for application in large clinical laboratories for automated rT3 assay. The methods provided are accomplished without the necessity of sample purification via solid phase extraction prior to liquid chromatography.

Suitable samples for use in methods of the present invention include any sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as blood, plasma, serum, saliva, cerebrospinal fluid, or a tissue sample. Such samples may be obtained, for example, from a patient; that is, a living person, male or female, presenting oneself in a clinical setting for diagnosis, prognosis, or treatment of a disease or condition. The sample is preferably obtained from a patient, for example, blood serum or plasma.

The present invention contemplates kits for a rT3 quantitation assay. A kit for a rT3 quantitation assay of the present invention may include a kit comprising an internal standard, in an amount sufficient for at least one assay. Typically, the kits will also include instructions recorded in a tangible form (e.g., contained on paper or an electronic medium) for using the packaged reagents for use in a measurement assay for determining the amount of rT3.

Calibration and QC pools for use in embodiments of the present invention can be prepared using "stripped" plasma or serum (stripped of rT3): for example, analyte-stripped, defibrinated and delipidized plasma/serum. All sources of human or non-human plasma or stripped serum should be checked to ensure that they do not contain measurable amounts of endogenous rT3.

Sample Preparation for Mass Spectrometry

Various methods may be used to enrich rT3 relative to other components (e.g. protein) in the sample prior mass spectrometry, including for example, liquid chromatography, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Protein precipitation is one preferred method of preparing a sample, especially a biological sample, such as serum or plasma. Protein precipitation may be used to remove at least a portion of the protein present in a sample leaving rT3 in the supernatant. Precipitated samples may be centrifuged to separate the liquid supernatant from the precipitated proteins; alternatively the samples may be filtered, for example through a glass fiber filter, to remove precipitated proteins. The resultant supernatant or filtrate may then be applied directly to mass spectrometry analysis; or alternatively to liquid chromatography and subsequent mass spectrometry analysis.

Various precipitation agents are known in the art, such as acetone, alcohols such as methanol, or various acidifying agents. In certain embodiments, the use of protein precipitation such as for example, methanol protein precipitation, may obviate the need for solid phase extraction (SPE) such as high turbulence liquid chromatography (HTLC), or other on-line extraction prior to mass spectrometry or HPLC and mass spectrometry.

Accordingly, in some embodiments, the method involves (1) performing a protein precipitation of the sample of interest; and (2) loading the supernatant directly onto the LC-mass spectrometer without using SPE.

In other embodiments, HTLC, alone or in combination with one or more purification methods, may be used to purify rT3 prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures may be linked in an automated fashion, the requirement for operator involvement during the purification of the analyte can be minimized. This feature may result in savings of time and costs, and eliminate the opportunity for operator error.

According to some embodiments, the method involves protein precipitation from serum or plasma samples. In these embodiments, a reagent which causes proteins to precipitate out of serum or plasma, such as methanol, acetonitrile, isopropanol, acetone, or zinc sulfate solution may be added, along with internal standard, to the sample in quantities sufficient to precipitate proteins from the sample. For example, methanol may be added to serum samples at a ratio within the range of about 1:1 to about 10:1; such as about 2:1 to about 5:1; such as about 3:1. After the proteins have been precipitated, the mixtures may then be centrifuged, with rT3 remaining in the supernatant. The supernatant may then be collected and subjected to mass spectrometric analysis, with or without further purification.

One additional such means of sample purification that may be used prior to mass spectrometry is liquid chromatography (LC). Liquid chromatography, including high-performance liquid chromatography (HPLC), relies on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with rT3. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample directly or indirectly (such as from a coupled SPE column) and an outlet port for discharging an effluent that includes the fractionated sample.

In one embodiment, the sample may be applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In some embodiments, HPLC is conducted with a hydrophobic column chromatographic system. In certain embodiments, a C18 analytical column (e.g., a Kinetex C18 with TMS endcapping analytical column from Phenomenex (2.6 µm particle size, 50×4.6 mm), or equivalent) is used. In certain embodiments, HTLC and/or HPLC are performed using HPLC Grade 0.1% aqueous formic acid and 100% methanol as the mobile phases.

Reverse phase HPLC is generally conducted with a non-polar stationary phase and an aqueous, moderately polar mobile phase. Under these conditions, samples injected for analysis which contain a large organic or alcohol solvent content pass over the stationary phase of the column without significant interaction, leading to poor column performance (i.e., less analyte retention and poor peak shape). One of two strategies is typically employed to counteract this effect. First, the samples comprising a high organic or alcohol content (such as those generated by alcohol protein precipitation) may be dried and reconstituted in a predominantly aqueous solvent. Second, very small volumes of samples comprising a high organic or alcohol content may be used, with the expectation that effects of such small absolute organic or alcohol volumes will largely be overcome because of the relative volumes of mobile phase to sample volume. Both approaches have significant detractors for clinical laboratory assays. Drying and reconstituting samples adds significant time and expense to what may otherwise be automated procedures, while use of very small sample volumes may diminish assay sensitivity by limiting the amount of analyte introduced to the column.

The present invention provides methods to overcome the above described complications. It has been found that a "plug" of aqueous or mostly aqueous solvent introduced to a reverse phase HPLC column immediately prior to introduction of a sample with a high organic or alcohol content avoids problems associated with such samples. The present methods may be applied to samples with at least 10%, 20%, 30%, 40%, 50%, 60%, 70%, 80%, 90%, 95%, or 100% (v/v) organic or alcohol, or mixtures thereof. In some embodiments, the sample solvent is methanol. For typical commercially available reverse-phase HPLC columns, an aqueous plug volume of about 10 µL to 1000 µL may be introduced immediately prior to about 10 µL to 1000 µL of a sample. Preferably the ratio of plug volume to sample volume will be in the range of about 5:1 to about 1:5; such as within the range of about 2:1 to about 1:2; such as about 1:1. Appropriate absolute and relative volumes of each solution will vary with variables such as the organic solvent content of the sample, the concentration of the analyte in the sample, column packing material, and column volume. However, it is within the skill of one skilled in the art to determine appropriate absolute and relative volumes of each solution.

Figure 1B:
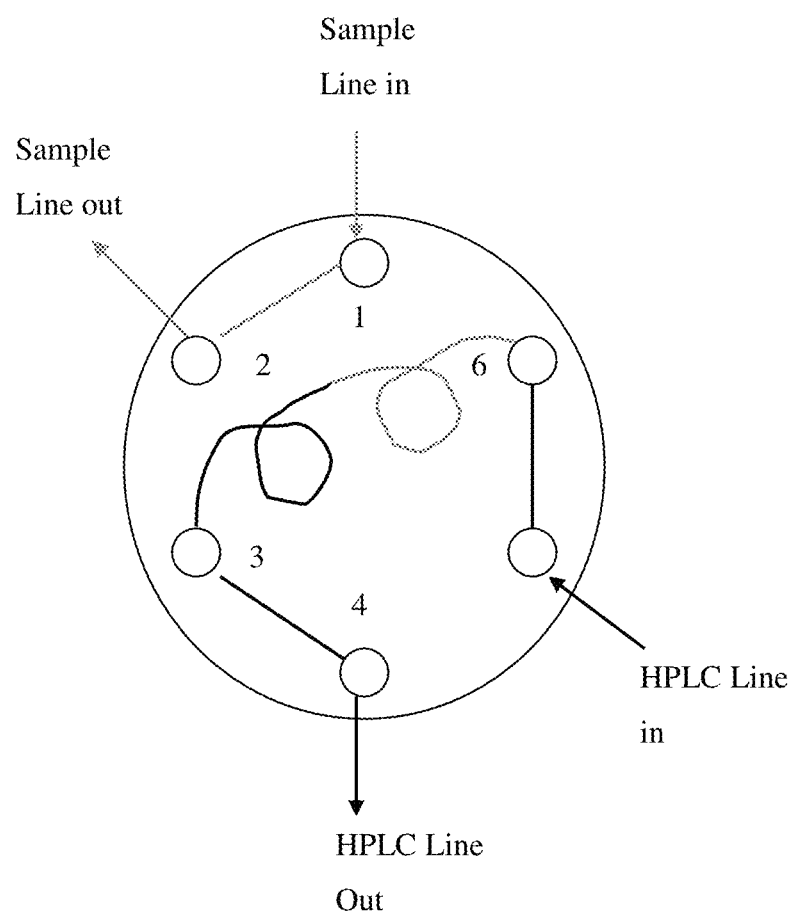
FIG. 1B shows ordered introduction of the fluid plugs into the HPLC.

The artisan will recognize that there are numerous ways to achieve the ordered introduction of multiple solutions onto an HPLC column using various configurations of plumbing and pumps. In some embodiments, a sample loop of a predetermined volume is used to achieve the ordered introduction of an aqueous plug, such as a plug that has no organic solvent component (i.e., a plug with a purely aqueous solvent component), prior to introduction of a sample comprising a high organic or alcohol solvent content. In these embodiments, the sample loop is initially filled with an aqueous fluid to capacity. A volume of organic or alcohol containing sample is then introduced into the sample loop such that the loop is only partially occupied by the organic or alcohol containing sample while at least some aqueous fluid remains in the loop. Then, a series of valves and pumps, or other plumbing components, is used to direct the aqueous plug followed by the organic or alcohol containing sample from the sample loop onto the HPLC column. FIGS. 1A and 1B show schematic representations of such a system in operation.

Once the analyte has been eluted from a first chromatography column, it may be subjected to further chromatography on one or more additional columns. By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

Detection and Quantitation by Mass Spectrometry

In various embodiments, rT3 present in a sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, rT3 is ionized by heated electrospray ionization (ESI) in negative mode.

In mass spectrometry techniques generally, after the sample has been ionized the positively charged or negatively charged ions thereby created may be analyzed to determine a mass-to-charge ratio. Suitable analyzers for determining mass-to-charge ratios include quadrupole analyzers, ion trap analyzers, magnetic and electric sector analyzers, and time-of-flight analyzers. The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of rT3. Methods of generating and using such standard curves are well known in the art and one of ordinary skill is capable of selecting an appropriate internal standard. For example, an isotopically labeled rT3 may be used as an internal standard; in certain preferred embodiments the standard is $^{13}C_6$-rT3. Numerous other methods for relating the amount of an ion to the amount of the original molecule will be well known to those of ordinary skill in the art.

One or more steps of the methods may be performed using automated machines. In certain embodiments, one or more purification steps are performed on-line.

In certain embodiments, such as MS/MS, where precursor ions are isolated for further fragmentation, collision activation dissociation is often used to generate the fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, rT3 is detected and/or quantified using MS/MS as follows. Samples are subjected to protein precipitation followed by liquid chromatography, preferably HPLC; the flow of liquid solvent from the liquid chromatography column enters an ESI nebulizer interface of an MS/MS analyzer; and the solvent/analyte mixture is converted to vapor in the heated tubing of the interface. The analyte (e.g., rT3), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of rT3. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral collision gas molecules and fragment. This process is called collision activated dissociation (CAD). The fragment ions generated are passed into quadrupole 3 (Q3), where the fragment ions of rT3 are selected while other ions are eliminated. In some embodiments, rT3 precursor ions are fragmented via collision with an inert collision gas such as argon or nitrogen, preferably nitrogen.

The methods may involve MS/MS performed in either positive or negative ion mode; preferably negative ion mode. Using standard methods well known in the art, one of ordinary skill is capable of identifying one or more fragment ions of a particular precursor ion of rT3 that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of rT3. As described above, the relative abundance of a given ion may be converted into an absolute amount of the original analyte, e.g., rT3, using calibration standard curves based on peaks of one or more ions of an internal molecular standard, such as $^{13}C_6$-rT3.

The following examples serve to illustrate the invention. These examples are in no way intended to limit the scope of the methods.

EXAMPLES

Example 1

Sample (Serum) and Reagent Preparation

Serum samples were prepared by collecting blood in a standard red-top serum Vacutainer® tube and allowed to clot at room temperature for 30 minutes. Samples were then centrifuged and the serum separated from the cells immediately. Alternately, blood was collected in a double-gel barrier tube, allowed to clot at room temperature. Samples were then centrifuged and the serum separated from the cells within 24 hours.

Plasma samples collected in EDTA plasma Vacutainer® tubes and sodium heparin Vacutainer® tubes were also prepared for analysis.

Three rT3 stock solutions were prepared. An initial rT3 stock solution of 1 mg/mL in methanol/basic solution was prepared by dissolving rT3 in 40 mL concentrated NaOH diluted to 100 mL with methanol. An intermediate stock solution of 1,000,000 pg/mL rT3 was prepared by further diluting a portion of the initial stock solution with methanol. Finally, a working stock solution of 10,000 pg/mL rT3 was prepared by further diluting a portion of the intermediate stock solution with double-stropped charcoal serum.

$^{13}C_6$-rT3 internal standard solutions were prepared similarly to the rT3 solutions described above, except that the final working $^{13}C_6$-rT3 internal standard was prepared to a final concentration of 500 pg/mL by dilution with methanol rather than stripped serum.

Example 2

Enrichment of rT3 in Serum by Protein Precipitation

100 μL of specimens were first added to a well in a 96 well plate. 300 μL of the 500 pg/mL $^{13}C_6$-rT3 in methanol solution (internal standard) was then added to each well, with each well checked for precipitate formation. After visually confirming precipitation, the well plate was mixed for about 1 minute at about 1500 rpm, allowed to rest, mixed again, refrigerated for about 30 minutes, and mixed a final time. After the final mix, the plate was centrifuged at a minimum of 3000×g for at least 30 minutes.

Example 3

Comparison of HPLC-MS/MS of rT3 in Methanol Solution with and without Leading Aqueous Plug Samples containing rT3 were prepared as indicated in Example 2 via methanol precipitation and via a similar procedure with acetone precipitation. The resulting samples contained a relatively high percent methanol or acetone as solvent.

100 μL of the methanol-solvent based samples were analyzed with and without introduction of an aqueous plug of about 100 μL to an HPLC analytical column (Phenomenex Kinetex C18 with TMS endcapping, 100×4.6 mm, 2.6 μm particle size column) immediately prior to introduction of the sample.

Figure 2A:
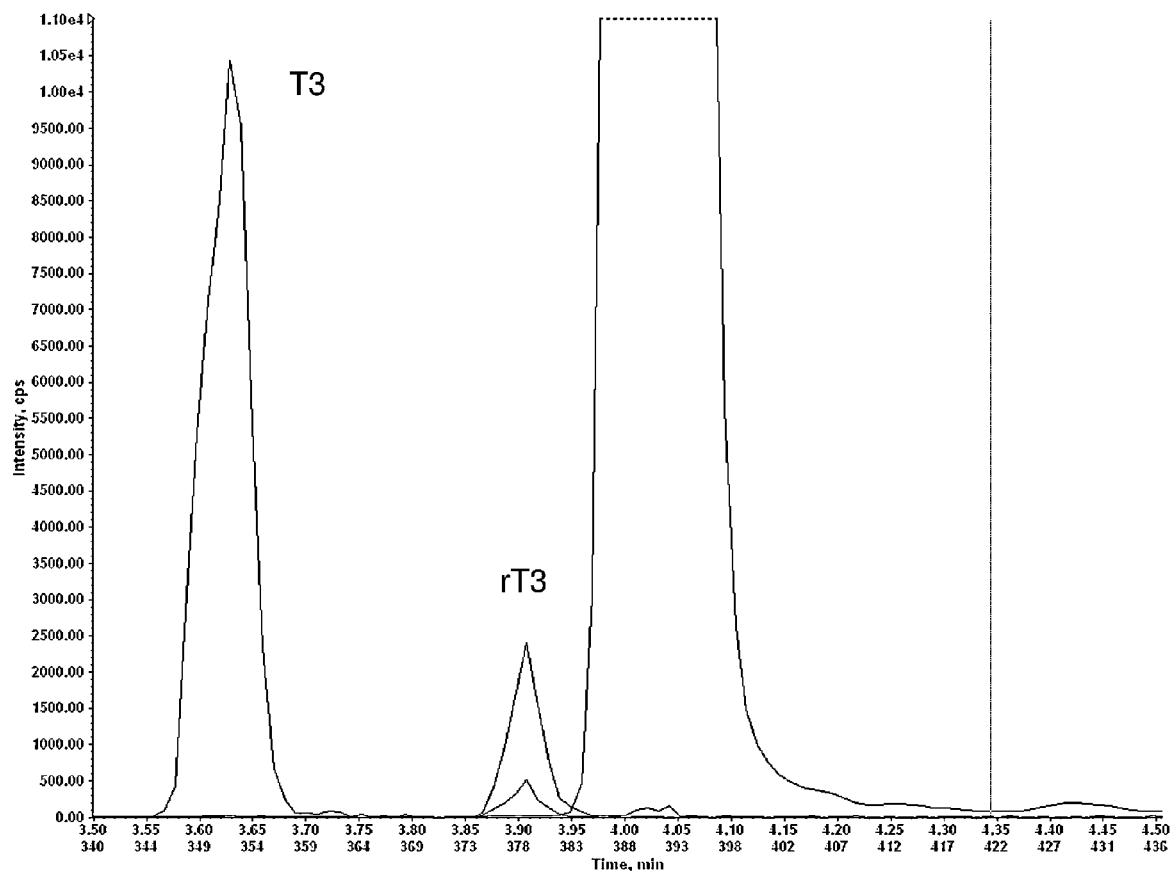
FIGS. 2A and B show exemplary chromatograms for T3 and rT3 in methanol-based samples collected by HPLC-MS/MS. The chromatograms were collected with (FIG. 2A) and without (FIG. 2B) introduction of an aqueous plug to the HPLC immediately prior to introduction of 100 µL of sample. Details are discussed in Example 3.
Figure 2B:
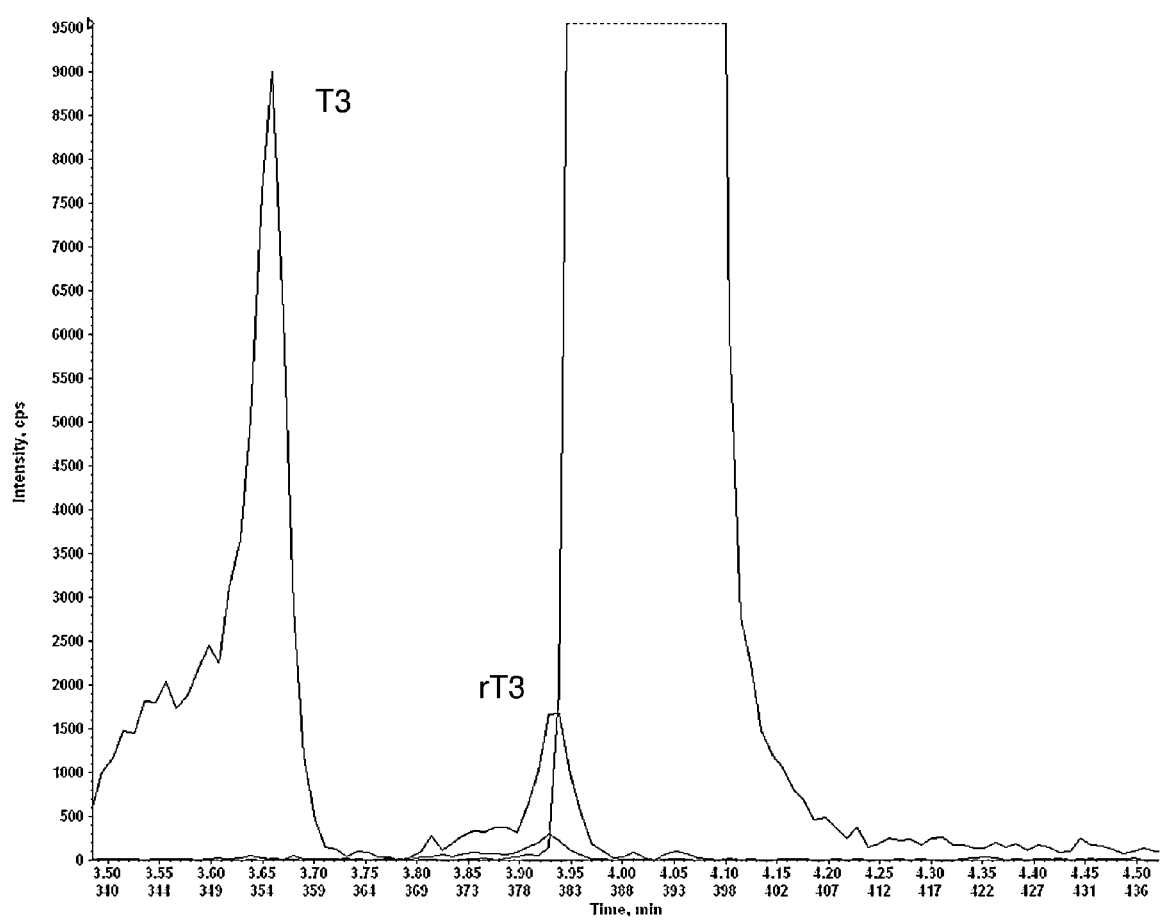

Mass chromatograms collected for both conditions are seen in FIGS. 2A-B. For comparison, 100 μL of an acetone-solvent based sample was also analyzed without introduction of an aqueous plug. An exemplary mass chromatogram for the acetone-based sample is seen in FIG. 3.

Figure 3:
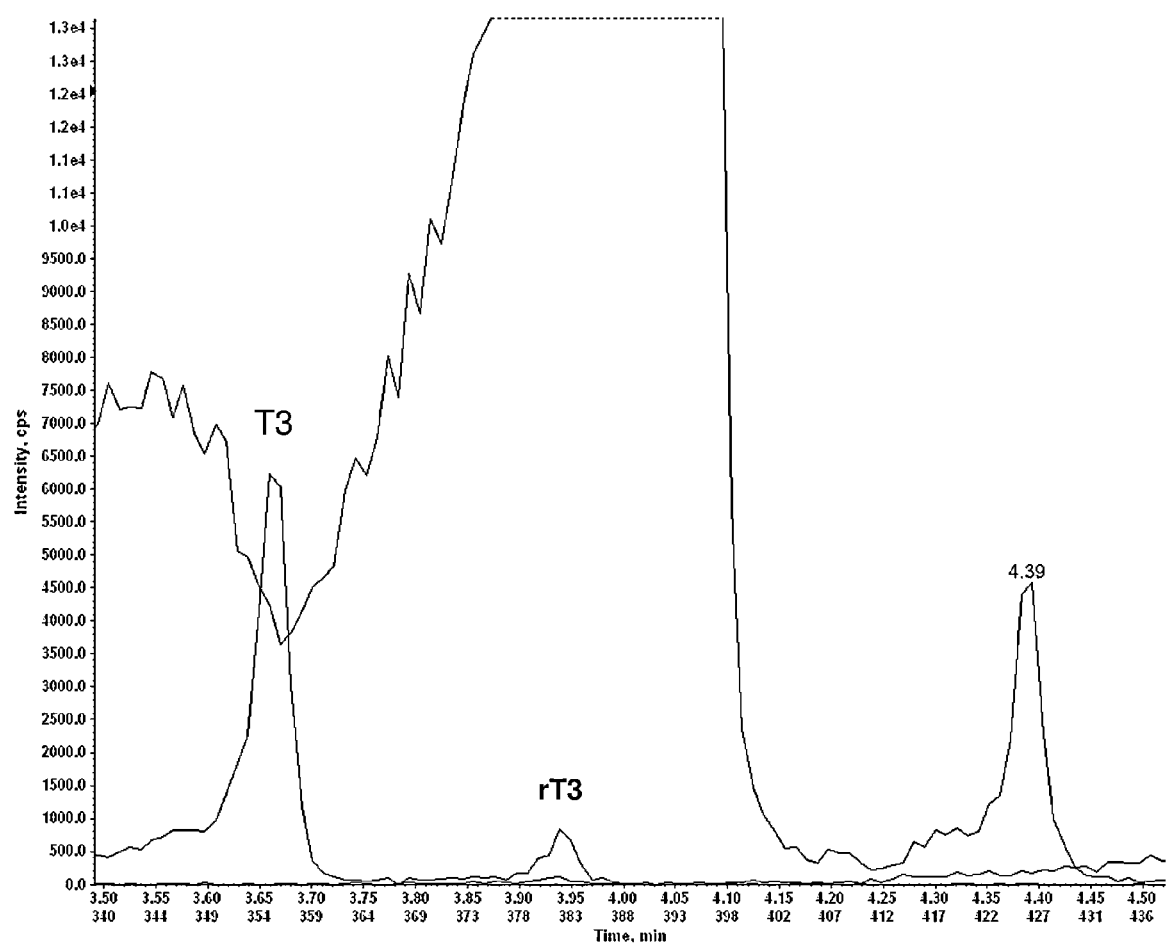
FIG. 3 shows exemplary chromatograms for T3 and rT3 in an acetone-based sample collected by HPLC-MS/MS. The chromatograms were collected without introduction of an aqueous plug to the HPLC immediately prior to introduction of 100 µL of sample. Details are discussed in Example 3.

As seen in FIGS. 2A-B and 3, the ion signal intensity for both T3 and rT3 was greatly enhanced for the sample purified via HPLC following introduction of an aqueous plug.

Example 4

Enrichment of rT3 Liquid Chromatography

The supernatants resulting from the centrifugation in Example 2 were subjected to high performance liquid chromatography for further enrichment of rT3 prior to mass spectrometric analysis. Sample injection was performed with a Cohesive Technologies Aria TLX-1 HTLC system operating in laminar flow mode using Aria OS V 1.5 or newer software.

The HTLC system automatically injected of 100 μL of the above prepared supernatants into the analytical column (Phenomenex Kinetex C18 with TMS endcapping, 100×4.6 mm, 2.6 μm particle size column). A binary HPLC gradient was applied to the analytical column, to separate rT3 from other analytes contained in the sample. Mobile phase A was 0.1% aqueous formic acid and mobile phase B was 100% methanol. The HPLC gradient started with a mixture of 70% mobile phase A and 30% mobile phase B, and was ramped to 5% mobile phase A and 95% mobile phase B over 300 seconds. This ratio was then held for an additional 60 seconds, before being returned to the original mixture for 60 seconds. Under these conditions, rT3 (and $^{13}C_6$-rT3) eluted off of the HPLC column at approximately 235 seconds. The eluted analytes were then subjected to MS/MS for quantitation.

Example 5

Detection and Quantitation of rT3 by MS/MS

MS/MS was performed using an ABSciex 5500 MS/MS system (ABSciex). The following software programs all from ABSciex were used in the Examples described herein: Analyst 1.4 or newer. Liquid solvent/analyte exiting the analytical HPLC column flowed to the ESI interface of the MS/MS analyzer. The solvent/analyte mixture was converted to vapor upon exit from the tubing of the interface. Analytes in the nebulized solvent were ionized by ESI in negative ion mode. Exemplary mass spectrometer parameters are shown in Table 1.

TABLE 1

Mass Spectrometer Operating Parameters

| Parameter | Value | Parameter | Value |
|---|---|---|---|
| Curtain Gas | 30.0 | Declustering Potential | −100.0 V |
| Collision Gas | 8 | Entrance Potential | −10.0 V |
| IonSpray Voltage | −2500 V | Collision Energy | −40.0 V |
| Temperature | 700.0° C. | Exit Lens | 10 V |
| Ion Source Gas 1 | 70.0 | Collision Cell Exit Potential | −10.0 V |
| Ion Source Gas 2 | 40.0 | | |

Ions passed to the first quadrupole (Q1), which selected ions with a mass to charge ratio of 649.9±0.50 for rT3 and 655.8±0.50 for $^{13}C_6$-rT3. Ions entering Quadrupole 2 (Q2) collided with nitrogen gas to generate ion fragments, which were passed to quadrupole 3 (Q3) for further selection. Simultaneously, the same process using isotope dilution mass spectrometry was carried out with an internal standard, $^{13}C_6$-rT3. The mass transitions used for detection and quantitation during validation on negative polarity are shown in Table 2. Additional mass transitions of 649.9±0.50→127.1±0.50 and 655.8±0.50→127.1±0.50 were observed for rT3 and $^{13}C_6$-rT3, respectively.

TABLE 2

Mass Transitions for rT3 (Negative Polarity)

| Analyte | Precursor Ion (m/z) | Production Ion (m/z) |
|---|---|---|
| rT3 | 649.9 ± 0.50 | 605.2 ± 0.50 |
| $^{13}C_6$-rT3 (internal standard) | 655.8 ± 0.50 | 611.1 ± 0.50 |

Figure 4A:
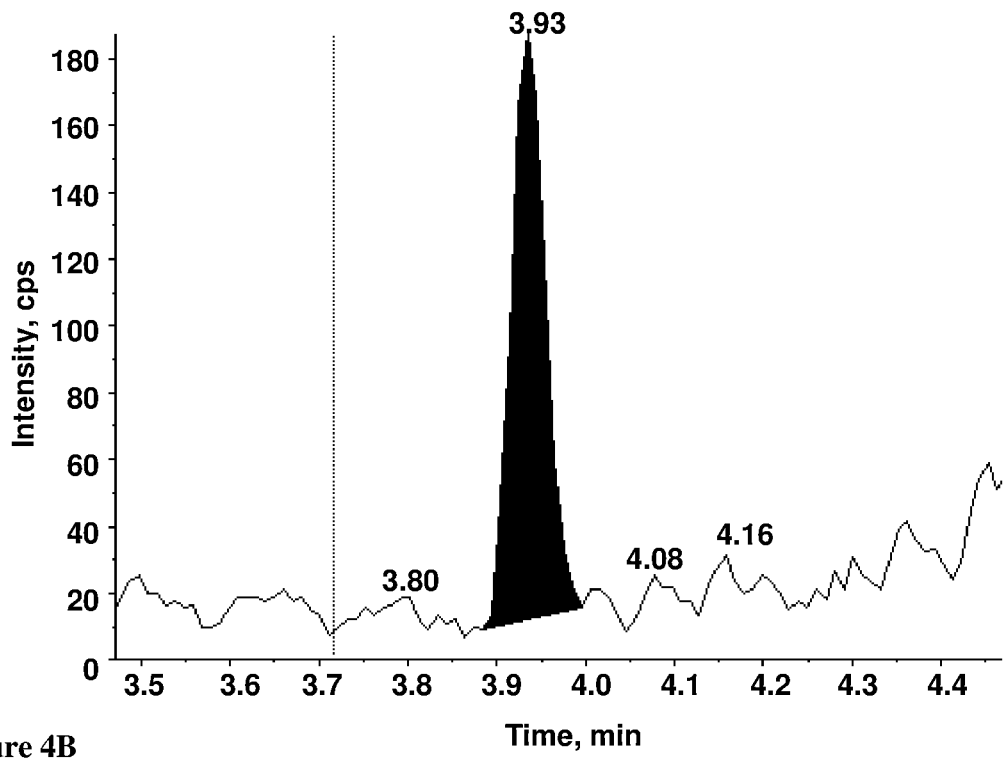
FIGS. 4A and B show exemplary chromatograms of rT3 and $^{13}C_6$-rT3 (internal standard), respectively. Details are discussed in Example 5.
Figure 4B:
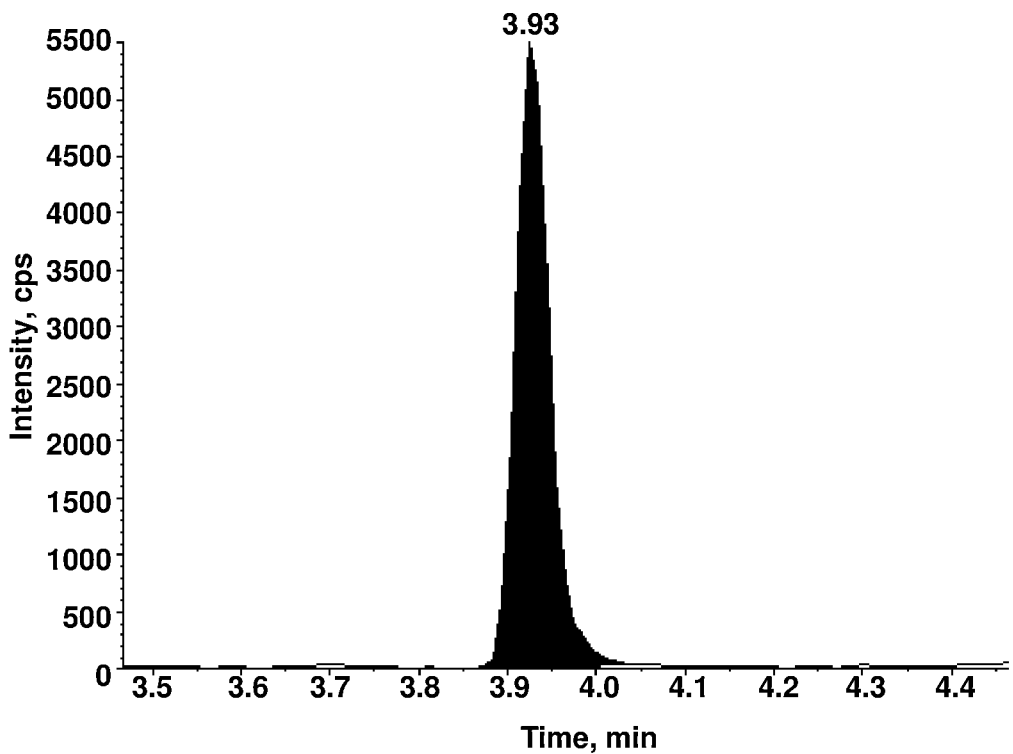

Exemplary chromatograms for rT3 and $^{13}C_6$-rT3 (internal standard) generated by monitoring the transitions shown in Table 2 are found in FIGS. 4A and B, respectively.

Example 6

Exemplary Calibration Curve Determination for rT3 by MS

Figure 5:
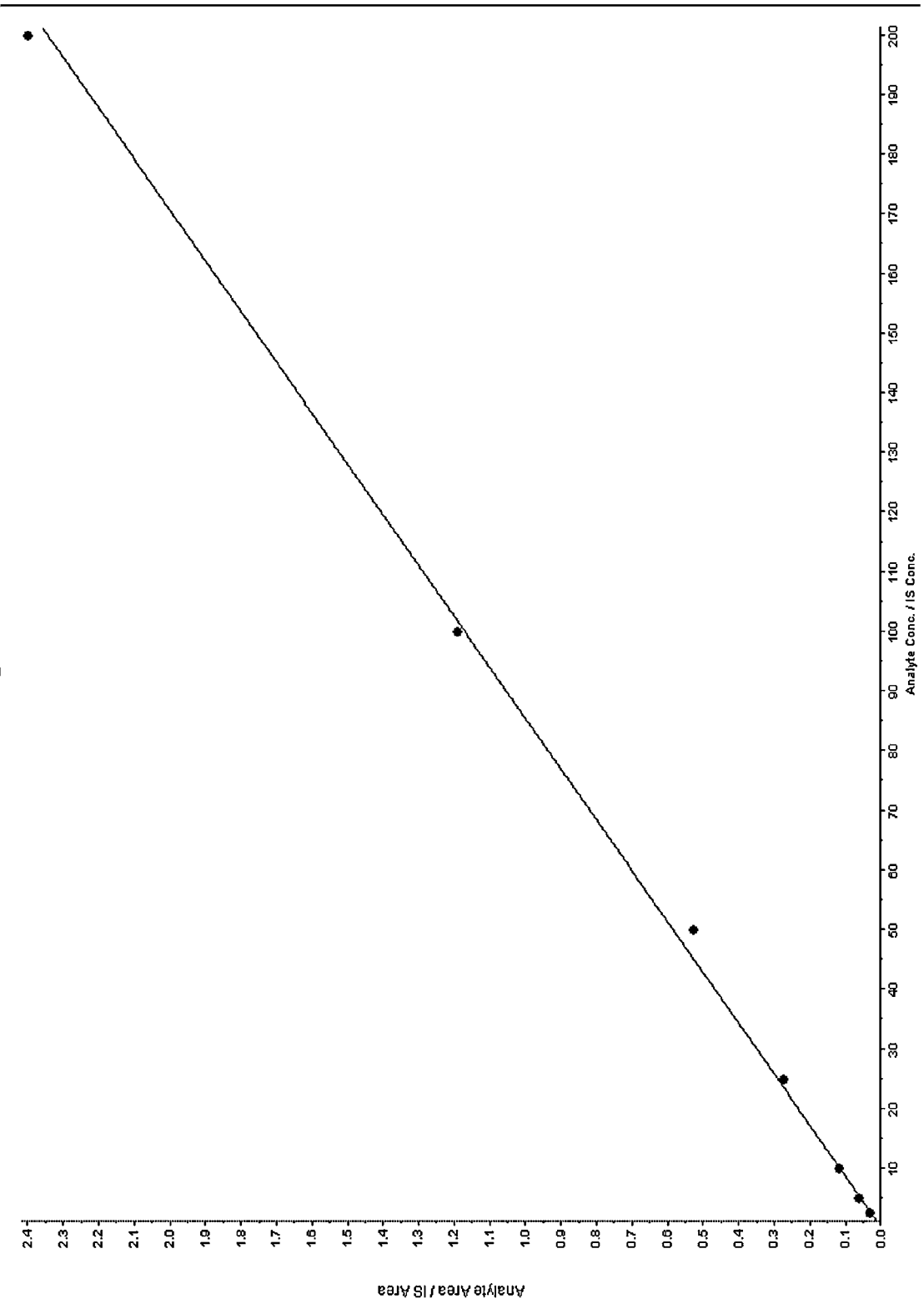
FIG. 5 shows a typical calibration curve generated by analyzing calibration samples with rT3 from 25 pg/mL to 2000 pg/mL. Details are described in Example 6.

Seven calibrator standards of rT3 in stripped serum at concentrations of 25 pg/mL, 50 pg/mL, 100 pg/mL, 250 pg/mL, 500 pg/mL, 1000 pg/mL, and 2000 pg/mL were prepared and analyzed as outlined above to generate an exemplary calibration curve. One such calibration curve is demonstrated in FIG. 5. The calibration curve shown was analyzed by linear regression, resulting in the following coefficients: y=0.0117x+−0.00213, and r=0.9988.

Example 7

Tests for Interfering Substances

Samples containing triglycerides (up to about 2000 mg/dL), bilirubin (up to about 50 mg/dL), and/or hemoglobin (up to about 500 mg/dL) were tested for possible interferences. No interference from these substances was detected.

Example 8 rT3 Assay Precision and Accuracy

Three quality control (QC) pools were prepared by spiking rT3 in stripped serum at 10 ng/dL, 25 ng/dL, and 100 ng/dL.

Five aliquots from each of the three QC pools were analyzed in each of five assays to determine the accuracy and coefficient of variation (CV (%)) of a sample within an assay. The data and results of these experiments are found in Table 3.

TABLE 3 rT3 Assay Precision and Accuracy

| | Run 1 | Run 2 | Run 3 | Run 4 | Run 5 |
|---|---|---|---|---|---|
| Level 1 (10 ng/dL) | | | | | |
| 1 | 10.60 | 10.30 | 10.20 | 9.73 | 10.10 |
| 2 | 10.90 | 9.81 | 10.40 | 10.50 | 10.00 |
| 3 | 10.20 | 9.63 | 9.39 | 9.77 | 9.67 |
| 4 | 10.00 | 10.00 | 10.00 | 9.67 | 9.45 |
| 5 | 10.60 | 9.58 | 10.60 | 10.50 | 9.97 |
| Count | 5 | 5 | 5 | 5 | 5 |
| Average | 10.46 | 9.86 | 10.12 | 10.03 | 9.84 |
| Within-Run (WR) SD | 0.36 | 0.29 | 0.46 | 0.43 | 0.27 |
| Level 2 (25 ng/dL) | | | | | |
| 1 | 26.00 | 23.80 | 25.80 | 24.90 | 24.70 |
| 2 | 24.50 | 24.60 | 24.70 | 24.60 | 26.10 |
| 3 | 24.60 | 25.30 | 25.40 | 24.60 | 25.30 |
| 4 | 25.10 | 25.00 | 25.40 | 26.60 | 24.40 |
| 5 | 25.50 | 24.00 | 24.80 | 25.00 | 23.90 |
| Count | 5 | 5 | 5 | 5 | 5 |
| Average | 25.14 | 24.54 | 25.22 | 25.14 | 24.88 |
| Within-Run (WR) SD | 0.63 | 0.64 | 0.46 | 0.84 | 0.85 |
| Level 3 (100 ng/dL) | | | | | |
| 1 | 100.00 | 95.10 | 99.80 | 95.30 | 98.50 |
| 2 | 97.30 | 97.00 | 98.30 | 98.60 | 96.80 |
| 3 | 97.70 | 95.30 | 101.00 | 103.00 | 96.50 |
| 4 | 102.00 | 95.10 | 102.00 | 97.90 | 97.40 |
| 5 | 94.20 | 97.20 | 98.70 | 98.60 | 98.10 |

TABLE 3-continued rT3 Assay Precision and Accuracy

| | | | | | |
|---|---|---|---|---|---|
| Count | 5 | 5 | 5 | 5 | 5 |
| Average | 98.24 | 95.94 | 99.96 | 98.68 | 97.46 |
| Within-Run (WR) SD | 2.95 | 1.06 | 1.55 | 2.77 | 0.84 |

| Summary | Level 1 | Level 2 | Level 3 |
|---|---|---|---|
| Count | 25 | 25 | 25 |
| Mean | 10.06 | 24.98 | 98.06 |
| Pooled WR SD | 0.37 | 0.70 | 2.03 |
| Pooled WR CV | 3.68% | 2.79% | 2.07% |
| Overall STD | 0.41 | 0.69 | 2.30 |
| Overall CV (%) | 4.06% | 2.75% | 2.34% |
| Target value | 10 | 25 | 100 |
| Accuracy (%) | 100.6% | 99.9% | 98.1% |

As shown in Table 3, the accuracy and coefficient of variation (CV (%)) at each QC level were acceptable for use as a clinical assay.

Example 9

Analytical Sensitivity: Limit of Blank (LOB), Limit of Detection (LOD) and Lower Limit of Quantitation (LLOQ)

The LLOQ refers to the concentration where measurements become quantitatively meaningful. The analyte response at the LLOQ is identifiable, discrete and reproducible at a concentration at which the standard deviation (SD) is less than one third of the total allowable error (TEa; arbitrarily set for rT3 as 30% of the LLOQ). The LOD is the concentration at which the measured value is larger than the uncertainty associated with it. The LOD is the point at which a value is beyond the uncertainty associated with its measurement and is defined as the mean of the blank plus four times the standard deviation of the blank. The LOB is set as two standard deviations above the mean measured value for a zero calibration standard.

Figure 6:
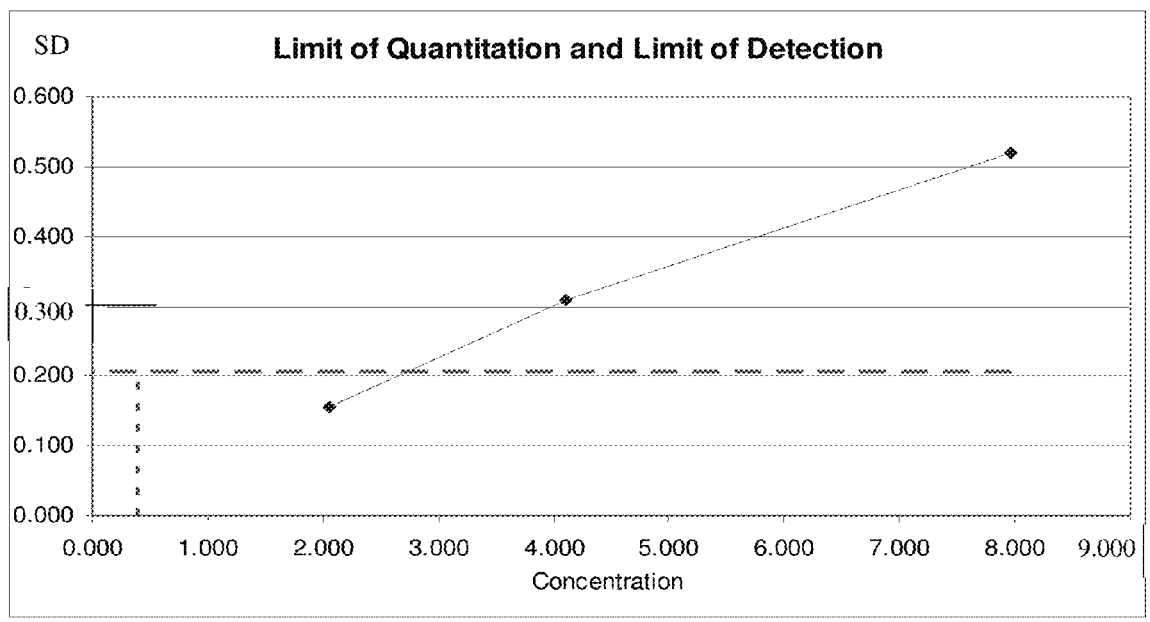
FIG. 6 shows a plot of data generated in lower limit of quantitation (LLOQ), limit of detection (LOD), and limit of blank (LOB) experiments. Details are described in Example 9.

The LLOQ, LOD, and LOB were determined by assaying samples at concentrations close to the expected LLOQ and determining the reproducibility (five replicates each at 0, 2, 4, and 8 ng/dL rT3 assayed in five runs) then determining the standard deviation (SD). The results were plotted for rT3 (shown in FIG. 6). The LOB, LOD, and LLOQ were determined to be from the curves to be 0.309 ng/dL, 0.392 ng/dL, and 2.050 ng/dL, respectively. Data from these experiments are presented in Table 4.

TABLE 4 rT3 Limit of Blank (LOB), Limit of Detection (LOD) and Lower Limit of Quantitation (LLOQ) Studies

| Run | Result | Pool A (2 ng/dL) | Pool B (4 ng/dL) | Pool C (8 ng/dL) | Zero Cal Std (0 ng/dL) |
|---|---|---|---|---|---|
| 1 | 1 | 2.330 | 3.870 | 7.940 | 0.224 |
| | 2 | 2.120 | 4.120 | 7.770 | 0.162 |
| | 3 | 1.960 | 3.810 | 7.600 | 0.229 |
| | 4 | 2.060 | 4.090 | 8.470 | 0.171 |
| | 5 | 1.990 | 4.190 | 8.070 | 0.282 |
| 2 | 1 | 2.010 | 4.230 | 8.100 | 0.252 |
| | 2 | 2.090 | 3.910 | 8.530 | 0.216 |
| | 3 | 2.170 | 4.340 | 8.440 | 0.251 |
| | 4 | 1.780 | 3.850 | 7.550 | 0.180 |
| | 5 | 2.120 | 4.190 | 7.990 | 0.149 |
| 3 | 1 | 2.170 | 4.380 | 7.520 | 0.213 |
| | 2 | 1.780 | 3.670 | 7.460 | 0.187 |
| | 3 | 2.080 | 3.920 | 8.310 | 0.222 |

TABLE 4-continued rT3 Limit of Blank (LOB), Limit of Detection (LOD) and Lower Limit of Quantitation (LLOQ) Studies

| Run | Result | Pool A (2 ng/dL) | Pool B (4 ng/dL) | Pool C (8 ng/dL) | Zero Cal Std (0 ng/dL) |
|---|---|---|---|---|---|
|   | 4 | 2.100 | 4.170 | 7.720 | 0.191 |
|   | 5 | 2.080 | 4.720 | 7.680 | 0.255 |
| 4 | 1 | 2.240 | 4.410 | 7.800 | 0.245 |
|   | 2 | 1.710 | 3.880 | 8.600 | 0.272 |
|   | 3 | 2.200 | 3.660 | 7.380 | 0.254 |
|   | 4 | 2.160 | 3.700 | 7.410 | 0.269 |
|   | 5 | 1.840 | 4.630 | 7.960 | 0.292 |
| 5 | 1 | 2.150 | 4.300 | 9.140 |   |
|   | 2 | 1.980 | 3.680 | 8.480 |   |
|   | 3 | 2.220 | 4.230 | 6.810 |   |
|   | 4 | 2.000 | 4.580 | 7.640 |   |
|   | 5 | 1.900 | 4.310 | 8.630 |   |
| Summary |||||||
| Count |  | 25 | 25 | 25 | 20 |
| Mean |  | 2.050 | 4.114 | 7.960 | 0.226 |
| SD |  | 0.156 | 0.309 | 0.520 | 0.042 |
| LOB |  |  |  |  | 0.309 |
| LOD |  |  |  |  | 0.392 |
| LOQ |  |  |  |  | 2.050 |

Example 10

Linearity and Assay Reference Interval

Figure 7:
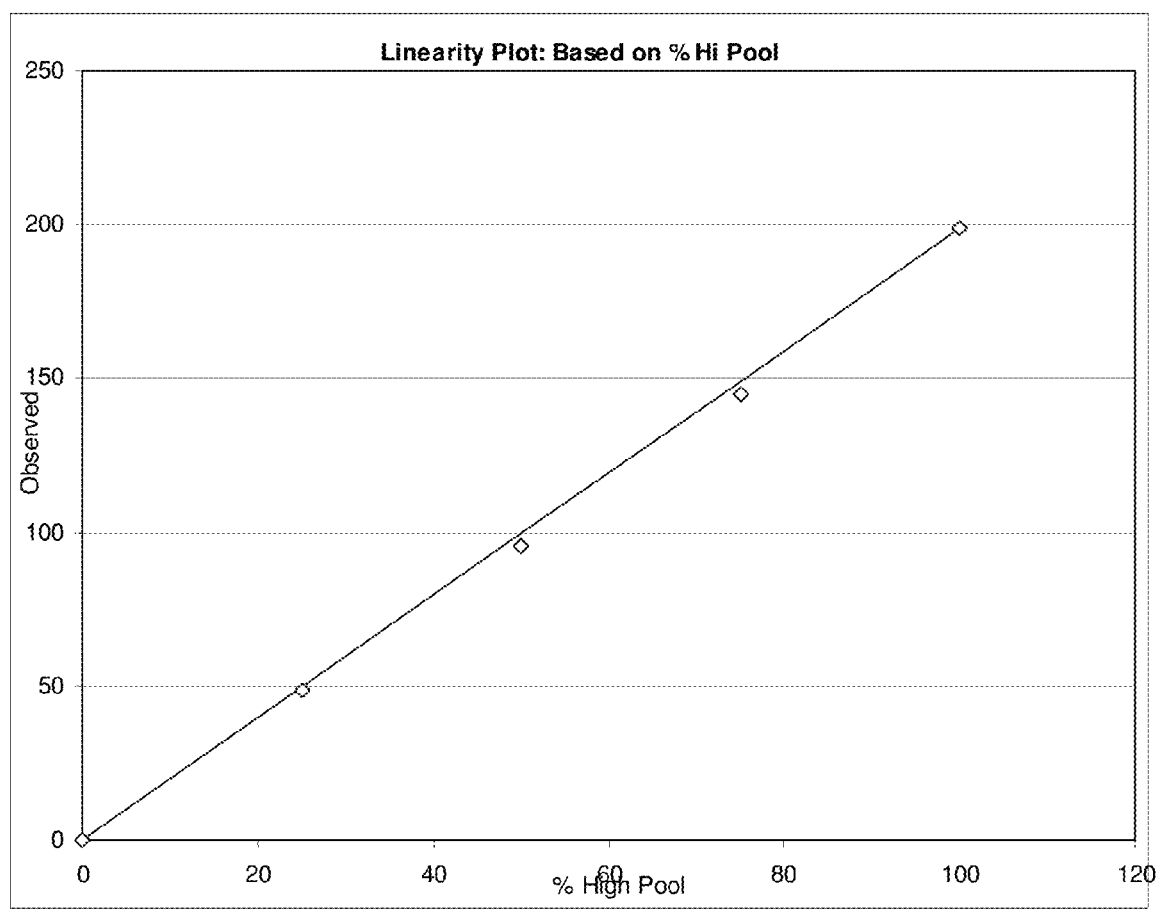
FIG. 7 shows linearity of rT3 detection to at least about 200 ng/dL. Details are described in Example 10.

To establish the linearity of rT3 detection, five samples were prepared from different proportions of blank striped serum and striped serum spiked with 200 ng/dL. Two duplicates of each sample ranging from 0% to 100% of the spiked serum were analyzed and the results plotted. A graph showing the linearity of resulting curve is shown in FIG. 7.

Reference interval studies were conducted by analyzing samples from 115 adults, including 61 females and 54 males between the ages of 18-86 years. The inclusion criteria were: apparently healthy, ambulatory, community dwelling, non-medicated adults. The exclusion criteria were normal TSH, FT4, FT3, anti-TPO and anti-TG, no history of chronic disease, medication or recent medical problems. The resulting data were analyzed to develop a normal reference interval. Results are presented in Table 5.

TABLE 5

Reference Interval

|  | rT3 (ng/dL) |
|---|---|
| Reference Interval Lower Limit | 7.000 |
| Reference Interval Upper Limit | 26.000 |
| Reference Interval Median | 15.000 |
| Number of donors | 115 |
| Number above RI | 5 |
| Number below RI | 3 |
| Percent outside RI | 7% |

Example 11

Sample Type Studies

Figure 8A:
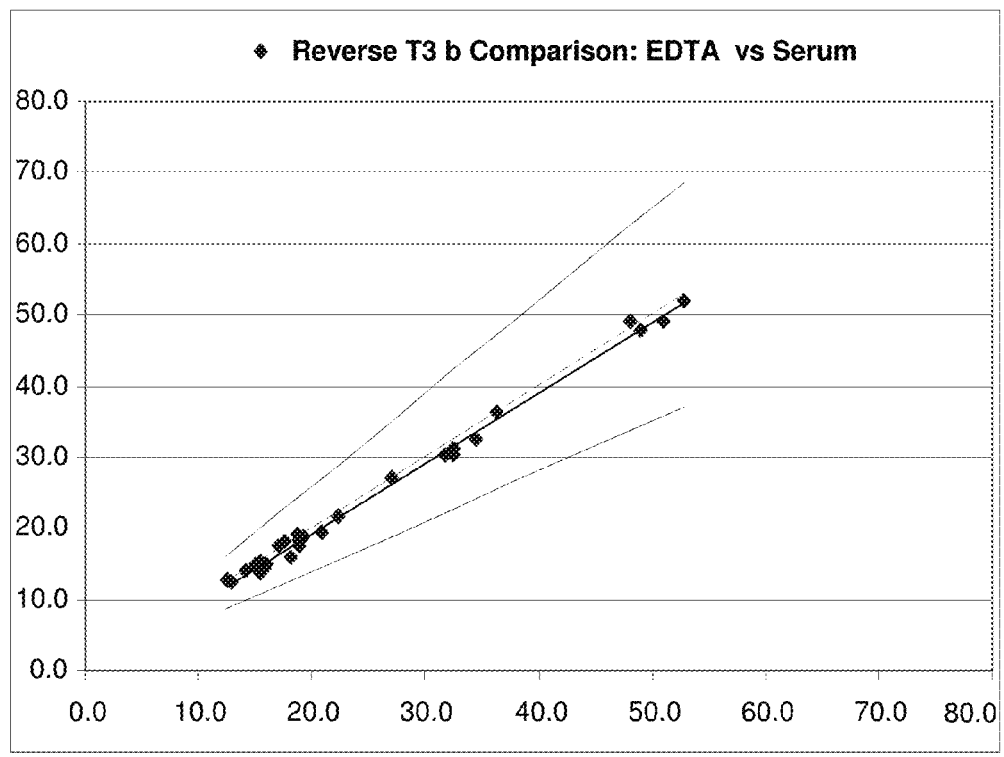
FIGS. 8A and B show comparison and difference plots, respectively, of rT3 quantitation in EDTA plasma and serum. Details are described in Example 11.
Figure 8B:
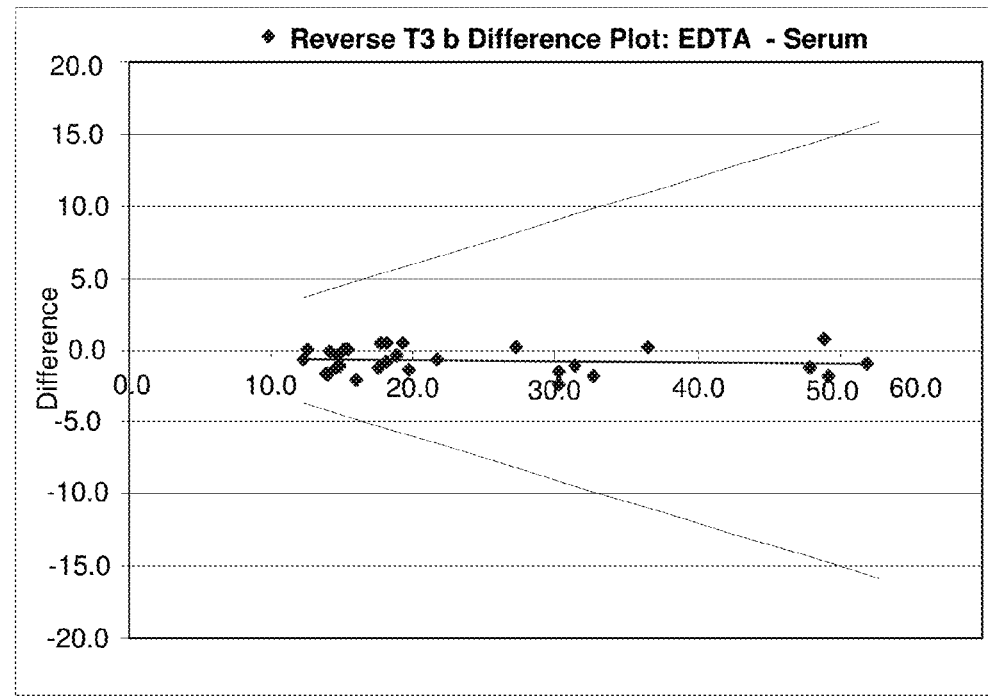
Figure 9A:
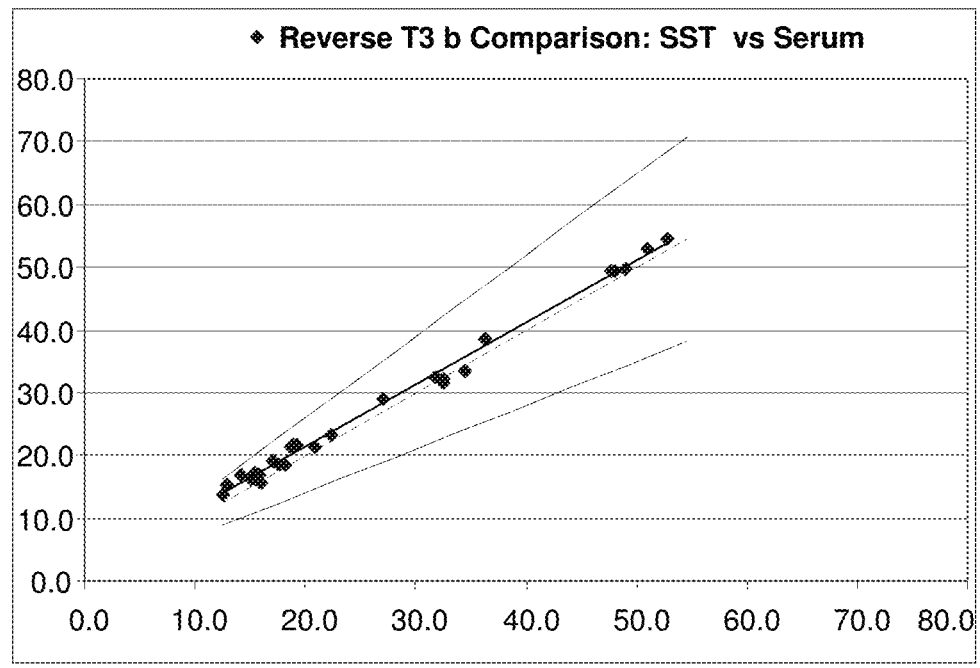
FIGS. 9A and B show comparison and difference plots, respectively, of rT3 quantitation in Heparin plasma and serum. Details are described in Example 11.
Figure 9B:
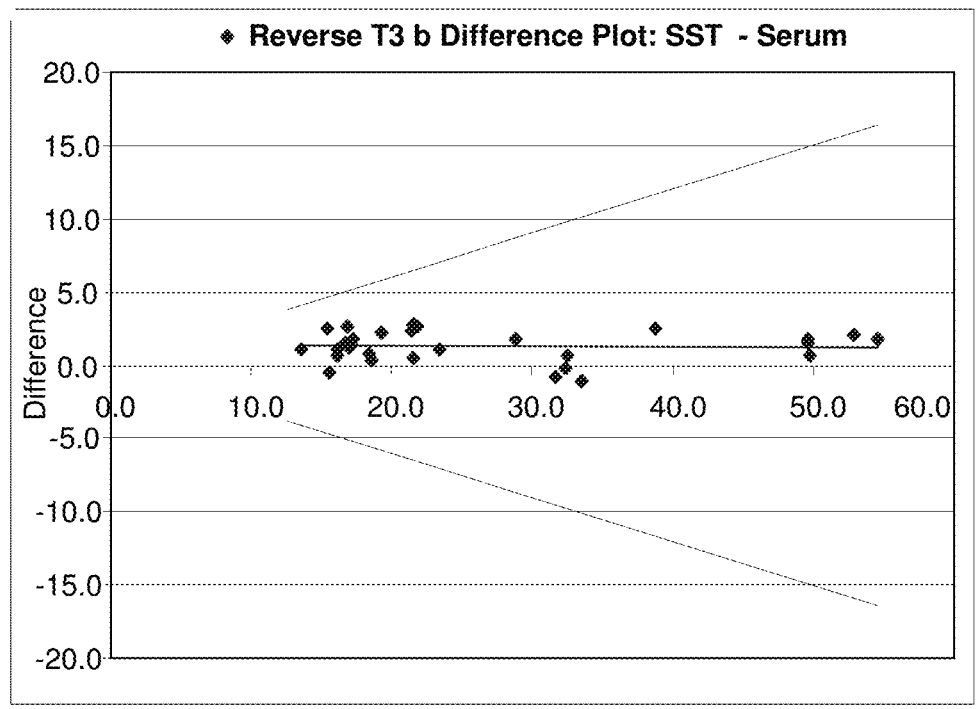
Figure 10A:
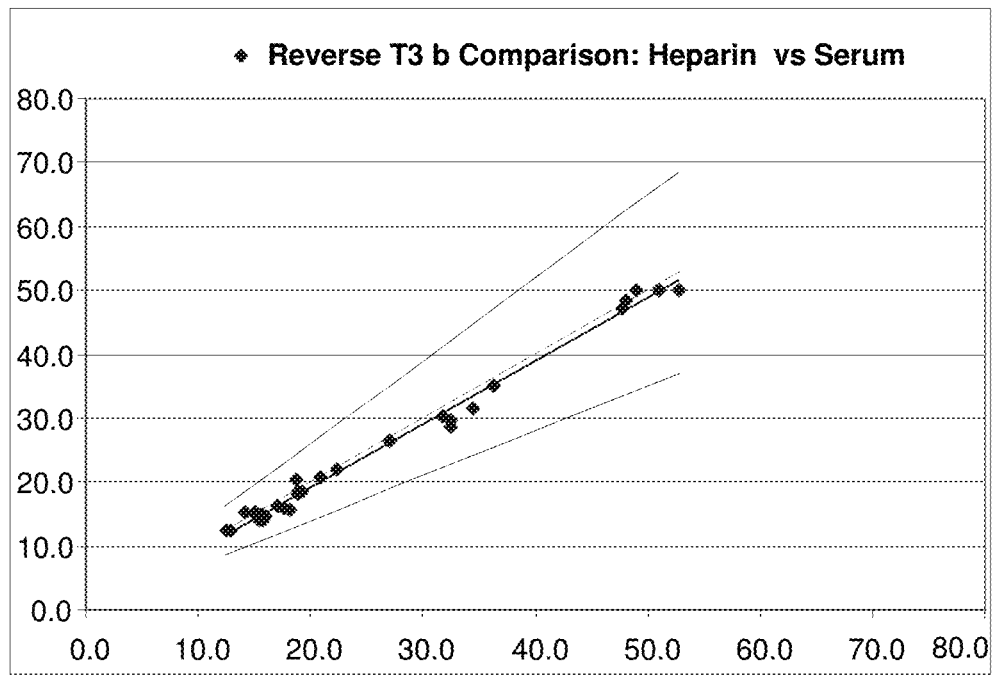
FIGS. 10A and B show comparison and difference plots, respectively, of rT3 quantitation in SST serum and serum. Details are described in Example 11.
Figure 10B:
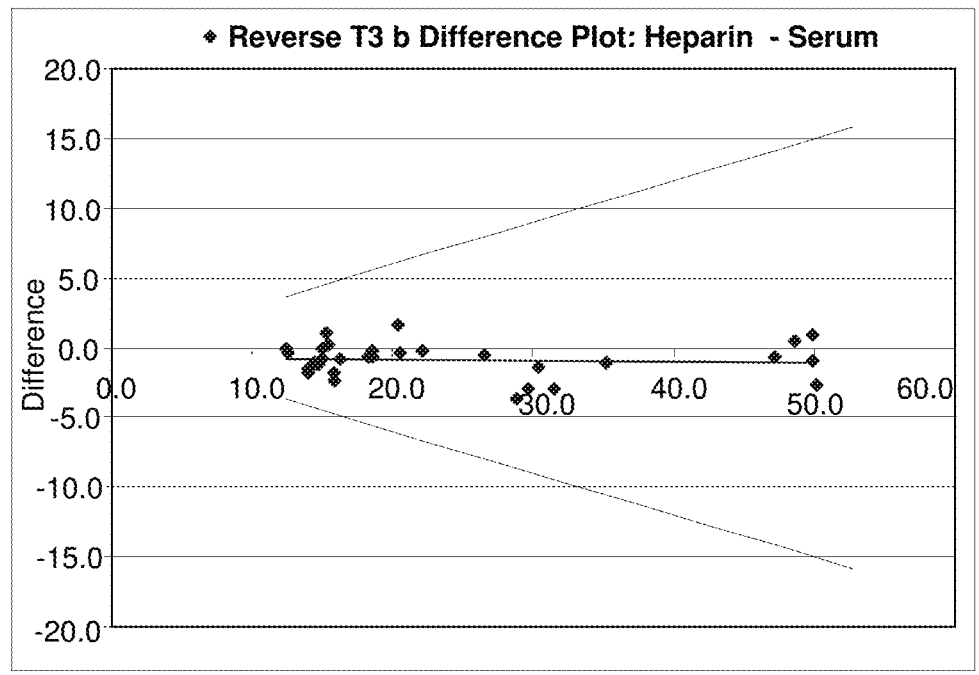

Samples from thirty patients were collected in various Vacutainer® Tubes to result in serum, EDTA plasma, Heparin Plasma, and serum from Serum Separation Tubes with gel barriers (i.e., SST sample tubes). The resulting samples were analyzed and the results compared. All sample types were determined to be acceptable for clinical analysis. Comparison plots of EDTA plasma, Heparin plasma, and SST serum samples versus serum are shown in FIGS. 8A, 9A, and 10A, respectively; difference plots are shown in FIGS. 8B, 9B, and 10B, respectively.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed:

1. A method for determining the amount of reverse triiodothyronine (rT3) in a sample by tandem mass spectrometry, said method comprising:
   a. subjecting the rT3 from the sample to liquid chromatography;
   b. ionizing rT3 from the sample and an internal standard to generate at least one rT3 ion and at least one internal standard ion detectable by tandem mass spectrometry;
   c. determining the amount of said at least one rT3 ion and the amount of said at least one internal standard ion by tandem mass spectrometry; and
   d. determining the amount of rT3 in the sample, comprising comparing the amount of said at least one rT3 ion and the amount of said at least one internal standard ion.

2. The method of claim 1, wherein liquid chromatography comprises high performance liquid chromatography (HPLC), reverse phase liquid chromatography (RPLC), reverse-phase high performance liquid chromatography (RP-HPLC), or high turbulence liquid chromatography (HTLC).

3. The method of claim 1, further comprising subjecting the sample to protein precipitation prior to liquid chromatography.

4. The method of claim 3, wherein said protein precipitation comprises organic solvent precipitation.

5. The method of claim 4, wherein said protein precipitation comprises methanol precipitation.

6. The method of claim 1, wherein said ionizing is by electrospray ionization (ESI) or atmospheric pressure chemical ionization (APCI).

7. The method of claim 1, wherein said ionizing is in positive ion mode.

8. The method of claim 1, wherein said ions are detected using multiple reaction monitoring (MRM).

9. The method of claim 1, wherein the one or more rT3 ions detectable by mass spectrometry comprise one or more selected from the group consisting of ions with a mass/charge ratio of 649.9±0.5, 605.2±0.5 and 127.1±0.5.

10. The method of claim 1, wherein the one or more rT3 ions detectable by mass spectrometry comprise one or more selected from the group consisting of ions with a mass/charge ratio of 649.9±0.5 and 605.2±0.5.

11. The method of claim 1, wherein the internal standard is isotopically labeled.

12. The method of claim 1, wherein the internal standard is isotopically labeled rT3.

13. The method of claim 1, wherein said sample comprises plasma or serum.

14. A method for determining the amount of reverse triiodothyronine (rT3) in a sample by tandem mass spectrometry, said method comprising:
   a. subjecting the rT3 from the sample to liquid chromatography;
   b. ionizing rT3 from the sample to generate at least one rT3 ion detectable by tandem mass spectrometry;
   c. determining the amount of said at least one rT3 ion by tandem mass spectrometry; and
   d. relating the amount of rT3 in the sample from the amount of said at least one rT3 ion.

15. The method of claim 14, wherein liquid chromatography comprises high performance liquid chromatography (HPLC), reverse phase liquid chromatography (RPLC), reverse-phase high performance liquid chromatography (RP-HPLC), or high turbulence liquid chromatography (HTLC).

16. The method of claim 14, further comprising subjecting the sample to protein precipitation prior to liquid chromatography.

17. The method of claim 16, wherein said protein precipitation comprises organic solvent precipitation.

18. The method of claim 16, wherein said protein precipitation comprises methanol precipitation.

19. The method of claim 14, wherein said ionizing is by electrospray ionization (ESI) or atmospheric pressure chemical ionization (APCI).

20. The method of claim 14, wherein said ionizing is in positive ion mode.

21. The method of claim 14, wherein said ions are detected using multiple reaction monitoring (MRM).

22. The method of claim 14, wherein the one or more rT3 ions detectable by mass spectrometry comprise one or more selected from the group consisting of ions with a mass/charge ratio of 649.9±0.5, 605.2±0.5 and 127.1±0.5.

23. The method of claim 14, wherein the one or more rT3 ions detectable by mass spectrometry comprise one or more selected from the group consisting of ions with a mass/charge ratio of 649.9±0.5 and 605.2±0.5.

24. The method of claim 14, wherein said sample comprises plasma or serum.

* * * * *